United States Patent
Kranzmann et al.

(10) Patent No.: US 11,464,725 B2
(45) Date of Patent: Oct. 11, 2022

(54) LIQUID PERSONAL CLEANSING COMPOSITION

(71) Applicant: Conopco, Inc., Englewood Cliffs, NJ (US)

(72) Inventors: Alyssa Nicole Kranzmann, Chicago, IL (US); Jamie Lynn Miller, North Haven, CT (US); Tirucherai Varahan Vasudevan, Bethany, CT (US)

(*) Notice: Subject to any disclaimer, the term of this patent is extended or adjusted under 35 U.S.C. 154(b) by 0 days.

(21) Appl. No.: 16/605,876

(22) PCT Filed: Apr. 11, 2018

(86) PCT No.: PCT/EP2018/059311
§ 371 (c)(1),
(2) Date: Oct. 17, 2019

(87) PCT Pub. No.: WO2018/206215
PCT Pub. Date: Nov. 15, 2018

(65) Prior Publication Data
US 2021/0045987 A1    Feb. 18, 2021

(30) Foreign Application Priority Data

May 8, 2017   (EP) .................................... 17169997

(51) Int. Cl.
| | | |
|---|---|---|
| *A61K 8/00* | (2006.01) | |
| *A61K 8/46* | (2006.01) | |
| *A61K 8/44* | (2006.01) | |
| *A61Q 5/02* | (2006.01) | |
| *A61Q 19/10* | (2006.01) | |

(52) U.S. Cl.
CPC .............. *A61K 8/463* (2013.01); *A61K 8/442* (2013.01); *A61K 8/447* (2013.01); *A61Q 5/02* (2013.01); *A61Q 19/10* (2013.01); *A61K 2800/48* (2013.01); *A61K 2800/596* (2013.01)

(58) Field of Classification Search
CPC ......... A61K 8/463; A61K 8/442; A61K 8/447
See application file for complete search history.

(56) References Cited

U.S. PATENT DOCUMENTS

| | | |
|---|---|---|
| 4,985,459 A | 1/1991 | Sunshine et al. |
| 5,009,814 A | 4/1991 | Kelkenberg et al. |
| 5,073,371 A | 12/1991 | Turner et al. |
| 5,073,372 A | 12/1991 | Turner et al. |
| 5,087,445 A | 2/1992 | Haffey et al. |
| 5,389,279 A | 2/1995 | Au et al. |
| 5,393,466 A | 2/1995 | Ilardi et al. |
| 5,415,810 A | 5/1995 | Lee |
| 5,952,286 A | 9/1999 | Puvvada et al. |
| 2013/0143784 A1 | 6/2013 | Rizk |
| 2013/0189212 A1 | 7/2013 | Jawale et al. |
| 2013/0189332 A1 | 7/2013 | Breyfogle |
| 2015/0297485 A1* | 10/2015 | Kleinen .................. A61K 8/37 514/786 |

FOREIGN PATENT DOCUMENTS

| | | |
|---|---|---|
| EP | 0556957 | 8/1993 |
| JP | 6404872 | 8/2016 |
| WO | WO2011117650 | 9/2011 |
| WO | WO2016079007 | 5/2016 |
| WO | WO2016147196 | 9/2016 |

OTHER PUBLICATIONS

Search Report and Written Opinion in EP17169997; dated Jul. 12, 2017.
Search Report and Written Opinion in PCTEP2018059311.
Written Opinion in PCTEP2018059311.
IPRP2 for PCTEP2018059311; Jun. 7, 2019.

* cited by examiner

*Primary Examiner* — Necholus Ogden, Jr.
(74) *Attorney, Agent, or Firm* — Edward A. Squillante, Jr.

(57) ABSTRACT

The invention relates to stable, mild and moisturizing lamellar liquid cleansing compositions which possess a lotion-like appearance conveying signals of enhanced moisturization. However, these liquids often are either unstable or cause poor lather production and other sensory deficits The use of a specific ratio of total acyl isethionates to acyl glutamates or other divalent anionic surfactant in a structured liquid product improve stability and lather production, mildness and acceptable odor.

16 Claims, No Drawings

LIQUID PERSONAL CLEANSING COMPOSITION

FIELD OF THE INVENTION

The present invention relates to liquid cleansing compositions suitable for topical application for cleansing the human body, such as the skin and hair. In particular, it relates to compositions which are preferably sulfate free and which are lamellar phase personal cleansing compositions. The compositions preferably are able to lather appreciably, are stable and are very mild. Preferably, they have an odor which is acceptable to the consumer.

BACKGROUND OF THE INVENTION

Consumers seek sulfate free personal cleansing compositions that are extremely mild and moisturizing while delivering superior sensory benefits such as creamy lather and soft, smooth skin typically after one shower. They should also have an acceptable odor. Acyl isethionates are known to be extremely mild surfactants and are an ideal surfactant for delivering mildness and moisturization to the consumer with a good-volume, creamy lather that is desirable. However, liquid cleansers containing high levels of fatty isethionates tend to crystallize due to the low solubility of acyl isethionates in water. Acyl glycinate, in combination with acyl isethionates, also provide very mild systems. These also can have unacceptable stability due to limited solubility of these surfactants in water. Using acyl isethionates having certain defined range of chain lengths (e.g., percentage of $C_{12}$ or below acyl isethionates) can resolve stability problems in acyl glycinate, acyl isethionate system but, applicants have found, can introduce problems relating to inadequate lather. Attempts to remedy lather issues (while maintaining stability) can further introduce other problems, such as unacceptable odor. It is thus extremely difficult to simultaneously achieve compositions which are mild, stable, have acceptable lather and have acceptable odor characteristics. Unexpectedly, it was found that for specific compositions comprising acyl isethionate and acyl glycinate, optionally in the presence of amphoteric surfactants, addition of acyl glutamate surfactant can allow simultaneously provision of mildness, stability, acceptable lather and acceptable odor if components are properly selected.

More specifically, these characteristics can be simultaneously met in compositions comprising (1) 1 to 10%, preferably 2 to 9% acyl isethionate and (2) 0.5 to 10%, preferably 0.5 to 8% acyl glycinate through the addition of (3) 1 to 10%, preferably 3 to 8% acyl glutamate and (4) optional amphoteric wherein (5) acyl glutamate comprises greater than 50% of the total of acyl isethionate and acyl glutamate combined; and (6) by further ensuring that overall content of acyl isethionate of chain length $C_{12}$ is between 60 to 100%, preferably 70 to 100%, more preferably 80 to 100%.

Mild liquid cleansers containing acyl isethionates are known.

U.S. Pat. No. 5,415,810 issued on May 16, 1995 to Robert S. Lee et al. discloses a detergent composition where the acyl isethionate is solubilized by the addition of a zwitterionic surfactant, and that the amount of zwitterionic surfactant must be half the weight percent of the acyl isethionate. There is no disclosure of specific acyl isethionate (of defined chain length), acyl glycinate, acyl glutamate systems of our invention.

Patent No. WO 2011/117650 issued on Sep. 29, 2011 to Stephen Moss O'Connor et. al. discloses concentrated surfactant compositions comprising acyl isethionate surfactants; most of these compositions are solid or paste at room temperature, and are only soluble/flowable at higher temperatures. Additionally, most of these compositions contain sulfate surfactants as solubilizers. Due to consumer's desire for sulfate free systems as well as the mildness that these sulfate free systems provide, such sulfate-containing systems are not preferred. Compositions of our invention are not contemplated.

U.S. Patent Publication No. 2013/0189212 issued on Jul. 25, 2013 to Arun Harachandra Jawale et al. discloses a surfactant composition comprising acyl isethionates in combination with acyl glycinates and alkyl betaine which is clear, concentrated and flowable; however it is reported that the pH of this system must be below pH 6. Acyl isethionates are prone to hydrolysis at non-neutral pH; therefore it is much more desirable for these systems to be stable around pH 7, in order to allow for long term stability. Further, specific ratios of acyl glutamate to acyl isethionate and specific acyl isethionates are not disclosed.

U.S. Patent Publication No. 2013/0143784 issued on Jun. 6, 2013 to Kirolos Rizk et al. discloses a composition that contains acyl isethionate, acyl glycinate, and cocamidopropyl betaine. Specific ratios of acyl glutamate to acyl isethionate and specific acyl isethionates are not disclosed.

Preferably, compositions of our invention are lamellar. Lamellar compositions show high zero-shear viscosity, which is favourable for deposition and/or structuring, while being very shear thinning, resulting in good dispensing when pouring the composition. In general, lamellar phase compositions are easy to identify, under cross-polarized microscopy, by their characteristic focal conic shape and oily streak texture while hexagonal phase exhibits angular fan-like texture. In contrast, micellar phases are optically isotropic.

It should be understood that lamellar phases may be formed in a wide variety of surfactant systems using a wide variety of lamellar phase "inducers" as described, for example, in U.S. Pat. No. 5,952,286 titled "Liquid Cleansing Composition Comprising Soluble, Lamellar Phase Inducing Structurant" by Sudhakar Puvvada, et al., issued Sep. 14, 1999. Generally, the transition from micelle to lamellar phase are functions of effective average area of headgroup of the surfactant, the length of the extended tail, and the volume of tail. Using branched surfactants or surfactants with smaller headgroups or bulky tails are also effective ways of inducing transitions from rod micellar to lamellar.

One way of characterizing lamellar dispersions include measuring viscosity at low shear rate (using for example a Stress Rheometer) when additional inducer (e.g., oleic acid or isostearic acid) is used. At higher amounts of inducer, the low shear viscosity will significantly increase.

Another way of measuring lamellar dispersions is using freeze fracture electron microscopy. Micrographs generally will show lamellar microstructure and close packed organization of the lamellar droplets (generally in size range of about 2 microns).

As indicated, none of the compositions disclosed above, or any other of which applicants are aware, disclose compositions in which ratio of acyl glutamate to acyl isethionate (in systems also comprising acyl glycinate and optional amphoteric) is specifically chosen and chain lengths distribution of acyl isethionate is specifically controlled to simultaneously provide compositions which are mild, are stable, have acceptable lather, and have acceptable odor.

SUMMARY OF THE INVENTION

One aspect of the invention is liquid, aqueous lamellar, personal cleansing compositions comprising:
1) 1 to 15%, preferably 1 to 10%, more preferably 2 to 8% by wt. $C_8$ to $C_{20}$ acyl isethionate;
2) 0.5% to 12%, preferably 1 to 10%, more preferably 1 to 8% or 1.5 to 7% by wt. acyl glycinate;
3) 0.5 to 12%, preferably 1 to 10%, or 1 to 8% by wt. acyl glutamate; and
4) 0 to 10%, preferably 0.5 to 5% or 1.0 to 4% by wt. of an amphoteric surfactant; and
5) preferably 0.1 to 10% by weight structurant
   wherein the amount by wt. of acyl glutamate in the composition, as active, is greater than 50% the amount by wt. of acyl isethionate; and
   wherein chain length distribution in the acyl isethionate is such that $C_{12}$ chain within the chain length distribution is between 60 to 100%, more preferably 70 to 100% and most preferably 80 to 100%.

Preferably, the amount of C12 to C18 chain length glycinate is predominant (greater than 50%, preferably greater than 60%, more preferably 65 to 100%, even more preferably 80 to 100% of total amount of C8, C10, and C12 to C18 chain length glycinate present. This further enhances the lather. Preferably, the C10 glycinate which is present is saturated decanoyl glycinate and the C10 glycinate is preferably substantially free of C10 glycinate with unsaturated bond, i.e. undecylenoyl glycine.

The combination of these features ensures that there is enough $C_{12}$ to ensure acceptable lather and odor characteristics and that, in combination with acyl glutamate, good stability is achieved. Thus, compositions are made stable, have acceptable lather (above 300 ml using Sita foam analysis as defined in the protocol) and have acceptable odor.

DETAILED DESCRIPTION OF THE INVENTION

Except in the examples, or where otherwise explicitly indicated, all numbers in this description indicating amounts of material or conditions of reaction, physical properties of materials and/or use are to be understood as modified by the word "about." All amounts are by weight of the final composition, unless otherwise specified.

It should be noted that in specifying any range of concentration or amount, any particular upper concentration can be associated with any particular lower concentration or amount.

For the avoidance of doubt, the word "comprising" is intended to mean "including" but not necessarily "consisting of" or "composed of." In other words, the listed steps or options need not be exhaustive.

The disclosure of the invention as found herein is to be considered to cover all embodiments as found in the claims as being multiply dependent upon each other irrespective of the fact that claims may be found without multiple dependency or redundancy.

In one form, the invention provides compositions which, based on specific selection of ratio of acyl glutamate to acyl isethionate and selection of chain length on acyl isethionate, provide compositions which are simultaneously mild, stable, have acceptable lather [above 300 ml using Sita foam analysis as defined in the protocol] and have acceptable odor.

Specifically, the composition comprises:
1) 1 to 15%, preferably 1 to 10%, more preferably 2 to 8% by wt. $C_8$ to $C_{20}$ acyl isethionate;
2) 0.5% to 12%, preferably 1 to 10%, more preferably 1 to 8% or 1.5 to 7% by wt. acyl glycinate;
3) 0.5 to 12%, preferably 1 to 10%, or 1 to 8% by wt. acyl glutamate; and
4) 0 to 10%, preferably 0.5 to 5% or 1.0 to 4% by wt. of an amphoteric surfactant; and
5) preferably 0.1 to 10% structurant
   wherein the amount by wt. of acyl glutamate in the composition, as active is greater than 50% the amount by wt. of acyl isethionate; and
   wherein chain length distribution in the acyl isethionate is such that $C_{12}$ chain within the chain length distribution is between 60 to 100%, more preferably 70 to 100%, and most preferably 80 to 100%.

Preferably acyl isethionate of chain length $C_{12}$ is 95% or above, more preferably 85% or above, most preferably 70% or above.

Preferably, the amount of C12 to C18 chain length glycinate is predominant (greater than 50%, preferably greater than 60%, more preferably 65 to 100%, even more preferably 80 to 100% of total amount of C8, C10, and C12 to C18 chain length glycinate present. Preferably, the C10 glycinate which is present is saturated decanoyl glycinate and the C10 glycinate is preferably substantially free of C10 glycinate with unsaturated bond, i.e. undecylenoyl glycine The compositions are described more specifically below.

Surfactants:

Mild anionic surfactants are preferably included in inventive cleansing composition. Preferably sulfate containing surfactants and soaps are present at levels below 3, 2 or 1 wt. % and preferably are not present. Surfactants are compounds that have hydrophobic and hydrophilic portions that act to reduce the surface tension of the aqueous solutions they are dissolved in. In addition to the isethionates, glycinates and glutamates which form inventive compositions, other useful surfactants which can be used include sulfosuccinates, sarcosinates, taurates, alaninates, threoninates, and blends thereof. Preferably harsh sulfate containing anionic surfactants such as SLES, SLS, Sodium Trideceth Sulfate, and soaps and blends thereof are present at maximum concentration levels of 3, 2 and 1 wt % and are preferably absent from the composition.

Anionic Surfactants:

The cleansing composition of the present invention preferably contains one or more non-soap, mild synthetic anionic detergents. Mild synthetic anionic surfactants are preferably used at levels as low as 5, 4, 3 and 2% by wt. and at levels as high as 8, 12, 16 and 20% by wt.

Solubilizing cations such as sodium, potassium, ammonium or substituted ammonium. Sodium and Potassium are preferred.

The inventive cleansing composition preferably contains $C_8$-$C_{18}$ acyl glycinate(s). These surfactants are prepared by reaction of $C_8$-$C_{18}$ fatty acid chloride with glycine in the presence of Sodium, Potassium, or ammonium hydroxide to form the corresponding $C_8$-$C_{18}$ acyl glycinate.

Preferred acyl isethionates include sodium lauroyl isethionate and sodium cocoyl isethionate.

Preferably, the amount of C12 to C18 chain length glycinate is predominant (greater than 50%, preferably greater than 60%, more preferably 65 to 100%. More preferably 80 to 100% of total amount of C8, C10, and C12 to C18 chain length glycinate present. While not wishing to be bound by theory, it is believed that predominance of C12 to C18 relative to C8 and C10 leads to enhanced lather. Preferably, any C10 glycinate which is present is saturated decanoyl glycinate and the 010 glycinate is preferably substantially free of C10 glycinate with unsaturated bond, i.e. undecylenoyl glycine.

Acyl glycinates are preferably present in an amount of 0.5 to 12%, preferably 1 to 10% by wt.

The inventive cleansing composition preferably contains $C_8$-$C_{18}$ acyl glutamate(s). These surfactants are prepared by reaction of $C_8$-$C_{18}$ fatty acid chloride with glutamic acid in the presence of Sodium, Potassium, or ammonium hydroxide to form the corresponding $C_8$-$C_{18}$ acyl glutamate. Preferred glutamates are potassium myristoyl glutamate and potassium cocoyl glutamate.

Acyl glutamates are preferably present in an amount of 0.5 to 12%, preferably 1 to 10% by wt.

The inventive cleansing composition preferably contains $C_8$-$C_{18}$ acyl isethionates. These esters are prepared by reaction between alkali metal isethionate with mixed aliphatic carboxylic acids having from 6 to 18 carbon atoms.

Acyl isethionates are preferably present in an amount of 1 to 10%, preferably 2 to 10% by wt. Overall content of isethionate of chain length $C_{12}$ within the chain length distribution of the acyl isethionate is between 60 to 100%, more preferably 70 to 100% and most preferably 80 to 100%. Acyl glutamate present, preferably 0.5 to 12% or 1 to 10% by wt. must comprise greater than 50% of acyl isethionate.

The acyl isethionate may be an alkoxylated isethionate such as is described in Ilardi et al., U.S. Pat. No. 5,393,466, titled Fatty Acid Esters of Polyalkoxylated isethonic acid; issued Feb. 28, 1995; hereby incorporated by reference. This compound has the general formula:

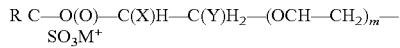
$SO_3M^+$ wherein R is an alkyl group having 8 to 18 carbons, m is an integer from 1 to 4, X and Y are hydrogen or an alkyl group having 1 to 4 carbons and $M^+$ is a monovalent cation such as, for example, sodium, potassium or ammonium.

A preferred combination is sodium lauroyl isethionate and potassium myristoyl glutamate. Another preferred combination is sodium cocoyl isethionate and potassium cocoyl glutamate.

Anionic detergent surfactant(s) which may be optionally used in the invention may be C8-C22 alkyl chains of: alkyl sulfosuccinates, methyl acyl taurates, acyl sarcosinates, acyl alaninates, acyl threoninates, alkylglycerylether sulfonates, alkyl sulfates, acyl lactylates, paraffin sulfonates, linear alkyl benzene sulfonates, alpha sulfo fatty acid esters, alkyl ether carboxylates, alkyl phosphate esters, ethoxylated alkyl phosphate esters, alpha olefin sulfates, and alkyl ether sulfates and mixtures thereof. The counterion of these surfactants is selected from: Na, K, $NH_4$, $N(CH_2CH_2OH)_3$.

Amphoteric Surfactants

One or more amphoteric surfactants are preferably used in this invention as a co-surfactant and stabilizer. Amphoteric surfactants are preferably used at levels as low as 3, 2, 1 or 0% by wt. and at levels as high as 4, 5 or 6% by wt.

Suitable amphoteric surfactants include simple betaines of formula:

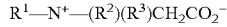

and amido betaines of formula:

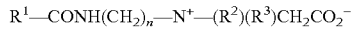

where n is 2 or 3.

In both formulae $R^1$, $R^2$ and $R^3$ are as defined previously. $R^1$ may in particular be a mixture of $C_{12}$ and $C_{14}$ alkyl groups derived from coconut oil so that at least half, preferably at least three quarters of the groups $R^1$ have 10 to 14 carbon atoms. $R^2$ and $R^3$ are preferably methyl.

A further possibility is that the amphoteric detergent is a sulphobetaine of formula:

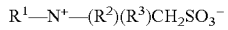

or

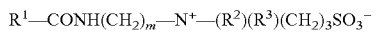

where m is 2 or 3, or variants of these in which $-(CH_2)_3 SO_3^-$ is replaced by

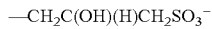

In these formulae $R^1$, $R^2$ and $R^3$ are as discussed previously.

Amphoacetates and diamphoacetates are also intended to be covered in possible zwitterionic and/or amphoteric compounds which may be used such as e.g., sodium lauroamphoacetate, sodium cocoamphoacetate, and blends thereof, and the like.

Amphoteric surfactants that are suitable include hydroxysultaines, betaines, and amphoacetates.

Preferred amphoterics include alkyl amidopropylbetaine, particularly cocoamidopropyl betaine; alkyl amidopropyl hydroxysultaine, particularly cocoamidopropylhydrosultaine; alkyl amphoacetate, particularly sodium lauromphoacetate and mixtures thereof.

Nonionic Surfactants

One or more nonionic surfactants may be used in the cleansing composition of the present invention as a co-surfactant. Nonionic surfactants are preferably used at levels as low as 3, 2, 1 or 0% by wt. and at levels as high as 4, 5 or 6% by wt. The nonionics which may be used include in particular the reaction products of compounds having a hydrophobic group and a reactive hydrogen atom, for example aliphatic alcohols, acids, amides or alkylphenols with alkylene oxides, especially ethylene oxide either alone or with propylene oxide. Specific nonionic detergent compounds are alkyl ($C_6$-$C_{22}$) phenols ethylene oxide condensates, the condensation products of aliphatic ($C_8$-$C_{18}$) primary or secondary linear or branched alcohols with ethylene oxide, and products made by condensation of ethylene oxide with the reaction products of propylene oxide and ethylenediamine. Other so-called nonionic detergent compounds include long chain tertiary amine oxides, long chain tertiary phosphine oxides and dialkyl sulphoxide, and the like.

Preferred nonionic surfactants include carboxylic acid/alcohol ethoxylates having the following structures:
a) HOCH2(CH2)n(CH2CH20)x H or
b) HOOC(CH2)m(CH2CH20)y H;
where m, n are independently<18; and x, y are independently>1. preferably m, n are independently 6 to 18; x, y are independently 1 to 30;
c) HOOC(CH2)i—CH=CH—(CH2)k(CH2CH2O)z H;
where i, k are independently 5 to 15; and z is independently 5 to 50. preferably i, k are independently 6 to 12; and z is independently 15 to 35.

The nonionic may also include a sugar amide, such as a polysaccharide amide. Specifically, the surfactant may be one of the lactobionamides described in U.S. Pat. No. 5,389,279 to Au et al. titled Compositions Comprising Nonionic Glycolipid Surfactants issued Feb. 14, 1995; which is hereby incorporated by reference or it may be one of the sugar amides described in U. S. Pat. No. 5,009,814 to Kelkenberg, titled "Use of N-Poly Hydroxyalkyl Fatty Acid Amides as Thickening Agents for Liquid Aqueous Surfactant Systems" issued Apr. 23, 1991; hereby incorporated into the subject application by reference.

Carboxylic Acids $C_{12}$-$C_{18}$ alkyl carboxylic acids are preferably used for the invention. Preferably carboxylic acid(s), such as lauric ($C_{12}$), myristic ($C_{14}$) or palmitic ($C_{16}$) acids are used alone or in combination. Advantageously the carboxylic acid(s) are used at levels as low as 2, 1 or 0% by wt. and at levels as high as 4, 5, or 6% by wt. Care should be taken not to increase lauric acid to a point where it inhibits lather of the surfactant as well as causing stability and crystallization problems.

Other structurants in addition to or in place of the normal carboxylic acids; starch, lauryl alcohol, PEG distearates, or polymeric thickeners may be used as structurants. Advantageously these structurants are used at levels as low as 3, 2, 1, 0% by wt. and at levels as high as 7, 8, 9, or 10% by wt.

Lamellar Structurants

As indicated, compositions of the invention are lamellar. Such compositions must have minimum of 0.1 or 1% or 2% lamellar structurant and maximum of 10% or 9% or 8% by wt., preferably 0.5 to 10 wt %, more preferably 1 to 5 wt % and most preferably 2 to 4 wt %.

Preferred lamellar structurants are selected from the group consisting of $C_8$ to $C_{18}$ alkyl fatty acid, alkyl alcohols and mixtures thereof. Particularly preferred are lauric acid, lauryl alcohol or mixtures thereof.

Cationic Skin Conditioning Agents

A useful component in compositions according to the invention is a cationic skin feel agent or polymer, such as for example cationic celluloses. Cationic polymers are preferably used at levels as low as about 0.1 to 2% up to levels as high as the solubility limit of the specific polymer, or preferably up to about 4 to 5% by wt., provided that the solubility limit of the particular cationic polymer or blend thereof is not exceeded.

Cationic cellulose is available from Amerchol Corp. (Edison, N.J., USA) in their Polymer JR (trade mark) and LR (trade mark) series of polymers, as salts of hydroxyethyl cellulose reacted with trimethyl ammonium substituted epoxide, referred to in the industry (CTFA) as Polyquaternium 10. Another type of cationic cellulose includes the polymeric quaternary ammonium salts of hydroxyethyl cellulose reacted with lauryl dimethyl ammonium-substituted epoxide, referred to in the industry (CTFA) as Polyquaternium 24. These materials are available from Amerchol Corp. (Edison, N.J., USA) under the tradename Polymer LM-200.

A particularly suitable type of cationic polysaccharide polymer that can be used is a cationic guar gum derivative, such as guar hydroxypropyltrimonium chloride (Commercially available from Rhone-Poulenc in their JAGUAR trademark series). Examples are JAGUAR C13S, which has a low degree of substitution of the cationic groups and high viscosity, JAGUAR C15, having a moderate degree of substitution and a low viscosity, JAGUAR C17 (high degree of substitution, high viscosity), JAGUAR C16, which is a hydroxypropylated cationic guar derivative containing a low level of substituent groups as well as cationic quaternary ammonium groups, JAGUAR 162 which is a high transparency, medium viscosity guar having a low degree of substitution, Jaguar Optima, which has a high degree of substitution and low molecular weight, and Jaguar Excel, which has a low degree of substitution and high viscosity.

Particularly preferred cationic polymers are JAGUAR C13S, JAGUAR C15, JAGUAR C17 and JAGUAR C16 and JAGUAR C162, especially JAGUAR C13S, JAGUAR C-14/BFG, Jaguar Optima and Jaguar Excel. The JAGUAR C14/BFG material is the same molecule as JAGUAR C13, except that a glyoxal cross linker has replaced the boron. Other cationic skin feel agents known in the art may be used provided that they are compatible with the inventive formulation.

Other suitable examples of surfactants described above which may be used are described in "Surface Active Agents and Detergents" (Vol. I & II) by Schwartz, Perry & Berch, incorporated into the subject application by reference in its entirety.

In addition, the inventive cleansing composition of the invention may include 0 to 15% by wt. optional ingredients as follows: perfumes; sequestering agents, such as tetrasodium ethylenediaminetetraacetate (EDTA), EHDP or mixtures in an amount of 0.01 to 1%, preferably 0.01 to 0.05%; and soluble coloring agents, opacifiers and the like; all of which are useful in enhancing the appearance or cosmetic properties of the product.

The compositions may further comprise antimicrobials such as caprylyl glycol, 2-hydroxy-4,2', 4' trichlorodiphenylether (DP300); preservatives such as methylisothiazolinone/methylchloroisothiazolinone (Kathon, MIT), dimethyloldimethylhydantoin/iodopropynyl butylcarbamate (Glydant XL1000), parabens, sorbic acid etc., and the like.

The compositions may also comprise coconut acyl mono- or diethanol amides as suds boosters, and strongly ionizing salts such as sodium chloride and sodium sulfate may also be used to advantage for increasing viscosity. Preferably strongly ionizing salts, otherwise known as electrolytes, will be present at less than 5, 4, 3, or 1% by wt.

Antioxidants such as, for example, butylated hydroxytoluene (BHT) and the like may be used advantageously in amounts of about 0.01% or higher if appropriate.

Emollients

The term "emollient" is defined as a substance which softens or improves the elasticity, appearance, and youthfulness of the skin (stratum corneum) by either increasing its water content, adding, or replacing lipids and other skin nutrients; or both, and keeps it soft by retarding the decrease of its water content.

Moisturizers that also are Humectants such as polyhydric alcohols, e.g. glycerin and propylene glycol, and the like; and polyols such as the polyethylene glycols such as Polyox WSR N-60K (PEG-45M) and the like are used in a preferred embodiment of the invention. Humectants are preferably used at a minimum of 3, 2, 1 or 0% by wt. and a maximum of 7, 8, 9 or 10% by wt.

Hydrophobic emollients with weight average particle sizes below either 1000 or 500 microns in diameter are defined herein as "finely dispersed oils" and are preferably used at a minimum of 3, 2, 1 or 0% by wt and a maximum of 20, 30, 40 or 50% by wt.

These hydrophobic emollients include but are not limited to the following:
  (a) silicone oils and modifications thereof such as linear and cyclic polydimethylsiloxanes; amino, alkyl, alkylaryl, and aryl silicone oils;
  (b) fats and oils including natural fats and oils (triglycerides) such as jojoba, soybean, sunflower, safflower, algal, rice bran, avocado, almond, olive, sesame, persic, castor, coconut, mink oils; cacao fat; beef tallow, lard;

hardened oils obtained by hydrogenating the aforementioned oils; and synthetic mono, di and triglycerides such as myristic acid glyceride and 2-ethylhexanoic acid glyceride;

(c) waxes such as carnauba, spermaceti, beeswax, lanolin, and derivatives thereof;

(d) hydrophobic plant extracts;

(e) hydrocarbons such as petrolatum, polybutene, liquid paraffins, microcrystalline wax, ceresin, squalene, pristan and mineral oil;

(f) higher alcohols such as lauryl, cetyl, stearyl, oleyl, behenyl, cholesterol and 2-hexydecanol alcohol;

(g) esters such as cetyl octanoate, myristyl lactate, cetyl lactate, isopropyl myristate, myristyl myristate, isopropyl palmitate, isopropyl adipate, butyl stearate, decyl oleate, cholesterol isostearate, glycerol monostearate, glycerol distearate, glycerol tristearate, alkyl lactate, alkyl citrate and alkyl tartrate;

(h) essential oils and extracts thereof such as mentha, jasmine, camphor, white cedar, bitter orange peel, ryu, turpentine, cinnamon, bergamot, citrus unshiu, calamus, pine, lavender, bay, clove, hiba, eucalyptus, lemon, starflower, thyme, peppermint, rose, sage, sesame, ginger, basil, juniper, lemon grass, rosemary, rosewood, avocado, grape, grapeseed, myrrh, cucumber, watercress, calendula, elder flower, geranium, linden blossom, amaranth, seaweed, ginko, ginseng, carrot, guarana, tea tree, jojoba, comfrey, oatmeal, cocoa, neroli, vanilla, green tea, penny royal, aloe vera, menthol, cineole, eugenol, citral, citronelle, borneol, linalool, geraniol, evening primrose, camphor, thymol, spirantol, penene, limonene and terpenoid oils;

(i) mixtures of any of the foregoing components, and the like.

Preferred emollients include petrolatum; natural wax; partially or fully hydrogenated triglyceride oils; and mixtures thereof. Preferred triglyceride oils include soybean oil or sunflower oil.

Thickeners

Compositions of the invention may be thickened. Examples of thickeners which may be used include polyethylene glycol distearates; starch; derivatives of starch; waxes; and polymeric thickeners. An example of a starch derivative is sodium hydroxyl propyl starch phosphate.

Optional Active Agents

Advantageously, active agents other than conditioning agents such as emollients or moisturizers defined above may be added to the cleansing composition in a safe and effective amount during formulation to treat the skin during the use of the product. Suitable active ingredients include those that are water soluble or are dispersible within the limits provided above. Suitable active agents may be advantageously selected from antimicrobial and antifungal actives, vitamins, anti-acne actives; anti-wrinkle, anti-skin atrophy and skin repair actives; skin barrier repair actives; non-steroidal cosmetic soothing actives; artificial tanning agents and accelerators; skin lightening actives; sunscreen actives; sebum stimulators; sebum inhibitors; anti-oxidants; protease inhibitors; skin tightening agents; anti-itch ingredients; hair growth inhibitors; 5-alpha reductase inhibitors; desquamating enzyme enhancers; anti-glycation agents; topical anesthetics, or mixtures thereof; and the like.

These active agents may be selected from water soluble active agents, oil soluble active agents, pharmaceutically-acceptable salts and mixtures thereof. Advantageously the agents will be soluble or dispersible in the cleansing composition. The term "active agent" as used herein, means personal care actives which can be used to deliver a benefit to the skin and/or hair and which generally are not used to confer a conditioning benefit, as is conferred by humectants and emollients previously described herein. The term "safe and effective amount" as used herein, means an amount of active agent high enough to modify the condition to be treated or to deliver the desired skin care benefit, but low enough to avoid serious side effects. The term "benefit," as used herein, means the therapeutic, prophylactic, and/or chronic benefits associated with treating a particular condition with one or more of the active agents described herein. What is a safe and effective amount of the active agent ingredient will vary with the specific active agent, the ability of the active to penetrate through the skin, the age, health condition, and skin condition of the user, and other like factors. Preferably the composition of the present invention comprises from about 0.01% to about 50%, more preferably from about 0.05% to about 25%, even more preferably 0.1% to about 10%, and most preferably 0.1% % to about 5%, by weight of the active agent component.

Anti-acne actives can be effective in treating acne vulgaris, a chronic disorder of the pilosebaceous follicles. Nonlimiting examples of useful anti-acne actives include the keratolytics such as salicylic acid (o-hydroxybenzoic acid), derivatives of salicylic acid such as 5-octanoyl salicylic acid and 4 methoxysalicylic acid, and resorcinol; retinoids such as retinoic acid and its derivatives (e.g., cis and trans); sulfur-containing D and L amino acids and their derivatives and salts, particularly their N-acetyl derivatives, mixtures thereof and the like.

Antimicrobial and antifungal actives can be effective to prevent the proliferation and growth of bacteria and fungi. Nonlimiting examples of antimicrobial and antifungal actives include b-lactam drugs, quinolone drugs, ciprofloxacin, norfloxacin, tetracycline, erythromycin, amikacin, 2,4, 4'-trichloro-2'-hydroxy diphenyl ether, 3,4,4'-trichlorobanilide, phenoxyethanol, triclosan; triclocarban; and mixtures thereof and the like.

Anti-wrinkle, anti-skin atrophy and skin repair actives can be effective in replenishing or rejuvenating the epidermal layer. These actives generally provide these desirable skin care benefits by promoting or maintaining the natural process of desquamation. Nonlimiting examples of antiwrinkle and anti-skin atrophy actives include vitamins, minerals, and skin nutrients such as milk, vitamins A, E, and K; vitamin alkyl esters, including vitamin C alkyl esters; magnesium, calcium, copper, zinc and other metallic components; retinoic acid and its derivatives (e.g., cis and trans); retinal; retinol; retinyl esters such as retinyl acetate, retinyl palmitate, and retinyl propionate; vitamin B 3 compounds (such as niacinamide and nicotinic acid), alpha hydroxy acids, beta hydroxy acids, e.g. salicylic acid and derivatives thereof (such as 5-octanoyl salicylic acid, heptyloxy 4 salicylic acid, and 4-methoxy salicylic acid); mixtures thereof and the like.

Skin barrier repair actives are those skin care actives which can help repair and replenish the natural moisture barrier function of the epidermis. Nonlimiting examples of skin barrier repair actives include lipids such as cholesterol, ceramides, sucrose esters, stearic acid and pseudo-ceramides as described in European Patent Specification No. 556,957; ascorbic acid; biotin; biotin esters; phospholipids, mixtures thereof, and the like.

Non-steroidal cosmetic soothing actives can be effective in preventing or treating inflammation of the skin. The soothing active enhances the skin appearance benefits of the present invention, e.g., such agents contribute to a more uniform and acceptable skin tone or color. Nonlimiting examples of cosmetic soothing agents include the following categories: propionic acid derivatives; acetic acid derivatives; fenamic acid derivatives; mixtures thereof and the like. Many of these cosmetic soothing actives are described in U.S. Pat. No. 4,985,459 to Sunshine et al., issued Jan. 15, 1991, incorporated by reference herein in its entirety.

Artificial tanning actives can help in simulating a natural suntan by increasing melanin in the skin or by producing the appearance of increased melanin in the skin. Nonlimiting examples of artificial tanning agents and accelerators include dihydroxyacetaone; tyrosine; tyrosine esters such as ethyl tyrosinate and glucose tyrosinate; mixtures thereof, and the like.

Skin lightening actives can actually decrease the amount of melanin in the skin or provide such an effect by other mechanisms. Nonlimiting examples of skin lightening actives useful herein include aloe extract, alpha-glyceryl-L-ascorbic acid, aminotyroxine, ammonium lactate, glycolic acid, hydroquinone, 4 hydroxyanisole, mixtures thereof, and the like.

Also useful herein are sunscreen actives. A wide variety of sunscreen agents are described in U.S. Pat. No. 5,087,445, to Haffey et al., issued Feb. 11, 1992; U.S. Pat. No. 5,073,372, to Turner et al., issued Dec. 17, 1991; U.S. Pat. No. 5,073,371, to Turner et al. issued Dec. 17, 1991; and Segarin, et al., at Chapter VIII, pages 189 et seq., of Cosmetics Science and Technology, all of which are incorporated herein by reference in their entirety. Nonlimiting examples of sunscreens which are useful in the compositions of the present invention are those selected from the group consisting of octyl methoxyl cinnamate (Parsol MCX) and butyl methoxy benzoylmethane (Parsol 1789), 2-ethylhexyl p-methoxycinnamate, 2-ethylhexyl N,N-dimethyl-p-aminobenzoate, p-aminobenzoic acid, 2-phenylbenzimidazole-5-sulfonic acid, oxybenzone, mixtures thereof, and the like.

Sebum stimulators can increase the production of sebum by the sebaceous glands. Nonlimiting examples of sebum stimulating actives include bryonolic acid, dehydroetiandrosterone (DHEA), orizanol, mixtures thereof, and the like.

Sebum inhibitors can decrease the production of sebum by the sebaceous glands. Nonlimiting examples of useful sebum inhibiting actives include aluminum hydroxy chloride, corticosteroids, dehydroacetic acid and its salts, dichlorophenyl imidazoldioxolan (available from Elubiol), mixtures thereof, and the like.

Also useful as actives in the present invention are protease inhibitors. Protease inhibitors can be divided into two general classes: the proteinases and the peptidases. Proteinases act on specific interior peptide bonds of proteins and peptidases act on peptide bonds adjacent to a free amino or carboxyl group on the end of a protein and thus cleave the protein from the outside. The protease inhibitors suitable for use in the present invention include, but are not limited to, proteinases such as serine proteases, metalloproteases, cysteine proteases, and aspartyl protease, and peptidases, such as carboxypepidases, dipeptidases and aminopepidases, mixtures thereof and the like.

Other useful as active ingredients in the present invention are skin tightening agents. Nonlimiting examples of skin tightening agents which are useful in the compositions of the present invention include monomers which can bind a polymer to the skin such as terpolymers of vinylpyrrolidone, (meth)acrylic acid and a hydrophobic monomer comprised of long chain alkyl (meth)acrylates, mixtures thereof, and the like.

Active ingredients in the present invention may also include anti-itch ingredients. Suitable examples of anti-itch ingredients which are useful in the compositions of the present invention include hydrocortisone, methdilizine and trimeprazineare, mixtures thereof, and the like.

Non-limiting examples of hair growth inhibitors which are useful in the compositions of the present invention include 17 beta estradiol, anti angiogenic steroids, curcuma extract, cycloxygenase inhibitors, evening primrose oil, linoleic acid and the like.

Suitable 5-alpha reductase inhibitors such as ethynylestradiol and, genistine mixtures thereof, and the like.

Non-limiting examples of desquamating enzyme enhancers which are useful in the compositions of the present invention include alanine, aspartic acid, N methyl serine, serine, trimethyl glycine, mixtures thereof, and the like.

A non-limiting example of an anti-glycation agent which is useful in the compositions of the present invention would be Amadorine (available from Barnet Products Distributor), and the like.

Solid Particulate Optical Modifiers

A useful optional component of compositions according to the present invention is that of solid particulate optical modifiers, preferably light reflecting platelet shaped or platy particles. These particles will preferably have an average particle size D50 ranging from about 25,000 to about 150,000 nm. For plate-like materials the average particle size is a number average value. The platelets are assumed to have a circular shape with the diameter of the circular surface averaged over many particles. The thickness of the plate-like particles is considered to be a separate parameter. For instance, the platelets can have an average particle size of 35,000 nm and an average thickness of 400 nm. For purposes herein, thickness is considered to range from about 100 to about 600 nm. Laser light scattering can be utilized for measurement except that light scattered data has to be mathematically corrected from the spherical to the non-spherical shape. Optical and electron microscopy may be used to determine average particle size. Thickness is normally only determined via optical or electron microscopy.

The refractive index of these particles may be at least about 1.8, generally from about 1.9 to about 4, e.g. from about 2 to about 3, and between about 2.5 and 2.8.

Illustrative but not limiting examples of light reflecting particles are bismuth oxychloride (single crystal platelets) and titanium dioxide and/or iron oxide coated mica. Suitable bismuth oxychloride crystals are available from EM Industries, Inc. under the trademarks Biron® NLY-L-2X CO and Biron® Silver CO (wherein the platelets are dispersed in castor oil); Biron® Liquid Silver (wherein the particles are dispersed in a stearate ester); and Nailsyn® IGO, Nailsyn® II C2X and Nailsyn® II Platinum 25 (wherein the platelets are dispersed in nitrocellulose). Most preferred is a system where bismuth oxychloride is dispersed in a $C_2$-$C_{40}$ alkyl ester such as in Biron® Liquid Silver.

Among the suitable titanium dioxide coated mica platelets are materials available from EM Industries, Inc. These include Timiron® MP-45 (particle size range 49,000-57,000 nm), Timiron® MP-99 (particle size range 47,000-57,000 nm), Timiron® MP-47 (particle size range 28,000-38,000 nm), Timiron® MP-149 (particle size range 65,000-82,000 nm), and Timiron® MP-18 (particle size range 41,000-51,000 nm). The weight ratio of titanium dioxide coating to the mica platelet may range from about 1:10 to about 5:1, preferably from about 1:6 to about 1:7, by weight. Advantageously the compositions will generally be substantially free of titanium dioxide outside of that required for coating mica.

Among the suitable iron oxide and titanium dioxide coated mica platelets are materials available from EM Industires, Inc. These include Timiron® MP-28 (particle size range 27,000-37,000 nm), Timiron® MP-29 (particle size range 47,000-55,000 nm), and Timiron® MP-24 (particle size range 56,000-70,000 nm).

Among the suitable iron oxide coated mica platelets are materials available from EM Industries, Inc. These include Colorona® Bronze Sparkle (particle size range 28,000-42,000 nm), Colorona® Glitter Bronze (particle size range 65,000-82,000 nm), Colorona® Copper Sparkle (particle size range 25,000-39,000 nm), and Colorona® Glitter Copper (particle size range 65,000-82,000 nm).

Suitable coatings for mica other than titanium dioxide and iron oxide may also achieve the appropriate optical properties required for the present invention. These types of coated micas must also meet the refractive index of at least about 1.8. Other coatings include silica on the mica platelets.

Exfoliants

The inventive composition may contain particles that are greater than 50 microns in average diameter that help remove dry skin. Not being bound by theory, the degree of exfoliation depends on the size and morphology of the particles. Large and rough particles are usually very harsh and irritating. Very small particles may not serve as effective exfoliants. Such exfoliants used in the art include natural minerals such as silica, talc, calcite, pumice, tricalcium phosphate; seeds such as rice, apricot seeds, etc; crushed shells such as almond and walnut shells; oatmeal; polymers such as polyethylene and polypropylene beads, flower petals and leaves; microcrystalline wax beads, synthetic wax beads, jojoba ester beads, and the like. These exfoliants come in a variety of particle sizes and morphology ranging from micron sized to a few mm. They also have a range of hardness. Some examples are given in table 1 below.

TABLE A

| Material | Hardness (Mohs) |
| --- | --- |
| Talc | 1 |
| Calcite | 3 |
| Pumice | 4-6 |
| Walnut Shells | 3-4 |
| Dolomite | 4 |
| Polyethylene | ~1 |

Compositions of the invention typically have viscosity in the range of 20,000 centipoise (cp) to 300,000 cp, preferably 50,000 to 200,000 cp, more preferably 80,000 to 160,000 cp as measured by Brookfield viscometer T-A. 0.5 rpm, 60 seconds.

Compositions have pH of 6.0 to 8.0, preferably 6.5 to 7.5, more preferably 6.7 to 7.3.

The invention will now be described in greater detail by way of the following non-limiting examples. The examples are for illustrative purposes only and not intended to limit the invention in any way. Physical test methods are described below:

Except in the operating and comparative examples, or where otherwise explicitly indicated, all numbers in this description indicating amounts or ratios of materials or conditions or reaction, physical properties of materials and/or use are to be understood as modified by the word "about".

Where used in the specification, the term "comprising" is intended to include the presence of stated features, integers, steps, components, but not to preclude the presence or addition of one or more features, integers, steps, components or groups thereof.

EXAMPLES

All percentages in the specification and examples are intended to be by weight unless stated otherwise.

Example 1

Several inventive and comparative compositions were prepared and the stability, odor production and lather profile was measured for each according to the methods provided below.

TABLE 1

| | Surfactant Chainlength Distributions | | | | | | | | | |
| --- | --- | --- | --- | --- | --- | --- | --- | --- | --- | --- |
| | Sodium Cocoyl Isethionate 1 | Sodium Cocoyl Isethionate 2 | Sodium Lauroyl Isethionate | Sodium Myristoyl Isethionate | Sodium Lauroyl Glycinate | Sodium Cocoyl Glycinate | Sodium Lauroyl Glutamate | Potassium Myristoyl Glutamate | Potassium Cocoyl Glutamate | Sodium Cocoyl Glutamate |
| C8 | 6% | 3% | 3% | | 6% | 7% | | | 6% | 6% |
| C10 | 6% | 2% | 2% | | 4% | 5% | | | 6% | 6% |
| C12 | 50% | 72% | 95% | | 90% | 78% | >95% | | 63% | 63% |
| C14 | 18% | 23% | | 100% | | 8% | | >95% | 20% | 20% |
| C16 | 10% | | | | | 2% | | | 4% | 4% |
| C18 | 10% | | | | | | | | <2% | <2% |

TABLE 2

Attempts to Solve Crystallization via lower Overall C12 in formulation

|  | Formula 1 | Formula 2 | Formula 3 | Formula 4 | Formula 5 |
|---|---|---|---|---|---|
| Sodium Cocoyl Glycinate | 4.7% | 4.7% | 4.7% | 4.7% | 4.7% |
| Sodium Cocoyl Isethionate 1 | 5.4% | 0% | 0% | 0% | 2.7% |
| Sodium Lauroyl Isethionate | 0% | 5.4% | 5.4% | 5.4% | 2.7% |
| Cocamidopropyl Betaine | 1.6% | 1.6% | 1.6% | 1.6% | 1.6% |
| Lauric Acid | 3% | 3% | 0% | 0% | 3% |
| Myristic Acid | 0% | 0% | 0% | 1.4% | 0% |
| Capric Acid | 0% | 0% | 2.8% | 1.4% | 0% |
| Lather Volume/Quality | Unacceptable | Acceptable | Acceptable | Acceptable | Unacceptable |
| Stability | Acceptable | Unacceptable | Acceptable | Acceptable | Acceptable |
| Odor | Acceptable | Acceptable | Unacceptable | Unacceptable | Acceptable |

Table 2 describes preliminary unsuccessful attempts to solve the crystallization of the high acyl-isethionate containing systems. It was observed that the use of sodium cocoyl isethionate 1 in Formula 1 resulted in acceptable stability as well as odor, however it is known that the C12 chainlength of these surfactants results in optimal lather volume, and the use of sodium cocoyl isethionate 1 resulted in unacceptable lather properties, specifically in lather volume. However, while the use of Sodium Lauroyl Isethionate in Formula 2 resulted in satisfactory lather properties the stability in terms of crystallization was unacceptable due to the high level of C12 chain lengths overall in the formulation, coming from the glyciante, isethionate, and Lauric acid (used to thicken and as a lamellar structurant). Formulae 3 and 4 were attempted in order to reduce the overall level of C12 chain length in the formulation, by removing the Lauric acid and replacing with capric and/or myristic acid. The addition of capric acid worked to solve the crystallization/stability, however the strong odor of the capric acid resulted in an unacceptable odor of the finished product. One further attempt to reduce the overall level of C12 chain length in the formulation was made in Formula 5, by using a combination of sodium cocoyl isethionate 1 and Sodium Lauroyl Isethionate, but while this resulted in positive stability and odor characteristics, the lather properties were unacceptable.

TABLE 3

|  | Formula 6 | Formula 7 | Formula 8 | Formula 9 | Formula 10 | Formula 11 |
|---|---|---|---|---|---|---|
| Sodium Cocoyl Glycinate | 2.35% | 2.35% | 2.35% | 2.35% | 2.35% | 0% |
| Sodium Lauroyl Glycinate | 0% | 0% | 0% | 0% | 0% | 2.35% |
| Sodium Lauroyl Isethionate | 5.4% | 0% | 0% | 0% | 0% | 0% |
| Sodium Cocoyl Isethionate 2 | 0% | 5.4% | 5.4% | 5.4% | 5.4% | 5.4% |
| Sodium Lauroyl Glutamate | 3.04% | 2.35% | 3.04% | 0% | 3.0% | 3.04% |
| Sodium Cocoyl Glutamate | 0% | 0% | 0% | 3.04% | 0% | 0% |
| Cocamidopropyl Betaine | 1.6% | 1.6% | 1.6% | 1.6% | 1.6% | 1.6% |
| Lauric Acid | 3.2% | 3.4% | 3.2% | 3.2% | 3.0% | 3.2% |
| Lather Volume/Quality | Acceptable | Acceptable | Acceptable | Acceptable | Acceptable | Acceptable |
| Stability | Unacceptable | Unacceptable | Acceptable | Acceptable | Acceptable | Acceptable |
| Odor | Acceptable | Acceptable | Acceptable | Acceptable | Acceptable | Acceptable |

Addition of Sodium Acyl Glutamates

Table 3 details the addition of Sodium Lauroyl glutamate and Sodium Cocoyl Glutamate to the formulation, as a replacement to a portion of the sodium acyl Glycinate. Unexpectedly, it was found that the addition of these acyl glutamates, which are divalent anionic surfactants, resulted in greater solubilization and stability of the acyl isethionate, while still imparting good lather and odor characteristics. It seem that in order to attain acceptable solubilization and stability, the divalent anionic acyl glutamate must be added in a quantity that is at least 50% of the quantity of acyl isethionate. There was still some insolubility observed using Sodium Lauroyl Isethionate, however the use of Sodium Cocoyl Isethionate 2, with a slightly lower level of C12 removed this crystallization, and in combination with the acyl glutamate, did not impact the lather attributes negatively.

TABLE 4

Addition of Potassium Acyl Glutamates

| | Form 12 | Form 13 | Form 14 | Form 15 | Form 16 | Form 17 | Form 18 | Form 19 | Form 20 | Form 21 |
|---|---|---|---|---|---|---|---|---|---|---|
| Sodium Cocoyl Glycinate | 2.35% | 2.35% | 2.35% | 0% | 2.35% | 0% | 0% | 0% | 0% | 0% |
| Sodium Lauroyl Glycinate | 0% | 0% | 0% | 2.35% | 0% | 2.35% | 2.35% | 2.35% | 2.35% | 2.35% |
| Sodium Lauroyl Isethionate | 0% | 0% | 0% | 0% | 5.4% | 0% | 0% | 0% | 0% | 0% |
| Sodium Cocoyl Isethionate 2 | 5.4% | 5.4% | 5.4% | 5.4% | 0% | 5.4% | 5.4% | 5.4% | 5.4% | 0% |
| Sodium Myristoyl Isethionate | 0% | 0% | 0% | 0% | 0% | 0% | 0% | 0% | 0% | 5.4% |
| Sodium Lauroyl Glutamate | 0% | 1.52% | 2.28% | 0% | 0% | 0% | 0% | 0% | 0% | 0% |
| Potassium Myristoyl Glutamate | 3.04% | 1.52% | 0.76% | 3.04% | 3.04% | 0% | 0% | 0% | 0% | 0% |
| Potassium Cocoyl Glutamate | 0% | 0% | 0% | 0% | 0% | 2.7% | 2.16% | 1.62% | 1.08% | 3.04% |
| Cocamidopropyl Betaine | 1.6% | 1.6% | 1.6% | 1.6% | 1.6% | 1.6% | 1.6% | 1.6% | 1.6% | 1.6% |
| Lauric Acid | 3.0% | 3.2% | 3.2% | 3.2% | 3.2% | 2% | 2% | 2% | 2% | 2.4% |
| Lather Volume/Quality | Acceptable | Acceptable | Acceptable | Acceptable | Acceptable | Acceptable | Acceptable | Acceptable | Acceptable | Acceptable |
| Stability | Acceptable | Acceptable | Acceptable | Acceptable | Acceptable | Acceptable | Acceptable | Acceptable | Acceptable | Acceptable |
| Odor | Acceptable | Acceptable | Acceptable | Acceptable | Acceptable | Acceptable | Acceptable | Acceptable | Acceptable | Acceptable |

Table 4 describes the addition of Potassium Acyl Glutamates to the high acyl-isethionate formulations. This resulted in even greater solubilization, allowing for the use of both Sodium Lauroyl Glycinate and Sodium Myristoyl Isethionate, and Sodium Lauroyl Isethionate with acceptable stability, odor and lather properties. The use of potassium acyl glutamates allows for less glutamate to be added in order to solubilize the acyl isethionates.

TABLE 5

Variation and Removal of Amphoteric Surfactant

| | Formula 9 | Formula 22 | Formula 23 | Formula 24 |
|---|---|---|---|---|
| Sodium Cocoyl Glycinate | 2.35% | 2.35% | 2.35% | 2.35% |
| Sodium Cocoyl Isethionate 2 | 5.4% | 5.4% | 5.4% | 5.4% |
| Sodium Cocoyl Glutamate | 3.04% | 3.04% | 3.04% | 3.04% |
| Cocamidopropyl Betaine | 1.6% | 0% | 0% | 0% |
| Cocamidopropyl Hydroxysultaine | 0% | 1.6% | 0% | 0% |
| Sodium Lauroamphoacetate | 0% | 0% | 1.6% | 0% |
| Lauric Acid | 3.2% | 3.2% | 3.0% | 2.4% |
| Lather Volume/Quality | Acceptable | Acceptable | Acceptable | Acceptable |
| Stability | Acceptable | Acceptable | Acceptable | Acceptable |
| Odor | Acceptable | Acceptable | Acceptable | Acceptable |

Table 5 demonstrates the flexibility of amphoteric surfactant, even to the point of removal. These variations show that, contrary to prior art, an amphoteric surfactant is not necessary for solubility or lather properties in the presence of glutamate surfactant.

TABLE 6

Variation and Removal of Monovalent Anionic Surfactant

|  | Formula 25 | Formula 26 | Formula 27 |
|---|---|---|---|
| Sodium Cocoyl Glycinate | 0% | 0% | 0% |
| Sodium Laureth Sulfate | 0% | 2.35% | 0% |
| Sodium Lauroyl Sarcosinate | 0% | 0% | 2.35% |
| Sodium Cocoyl Isethionate 2 | 5.4% | 5.4% | 5.4% |
| Sodium Cocoyl Glutamate | 5.4% | 3.04% | 3.04% |
| Cocamidopropyl Betaine | 0% | 0% | 0% |
| Cocamidopropyl Hydroxysultaine | 0% | 1.6% | 0% |
| Sodium Lauroamphoacetate | 0% | 0% | 1.6% |
| Lauric Acid | 2.4% | 2.4% | 2.4% |
| Lather Volume/Quality | Acceptable | Acceptable | Acceptable |
| Stability | Acceptable | Acceptable | Acceptable |
| Odor | Acceptable | Acceptable | Acceptable |

Table 6 demonstrates the flexibility of the monovalent anionic surfactant, up to and including full removal of the monovalent anionic surfactant in favor of acyl glutamate.

TABLE 7

Variation of divalent anionic surfactant

|  | Formula 28 | Formula 29 |
|---|---|---|
| Sodium Cocoyl Glycinate | 2.35% | 0% |
| Sodium Cocoyl Isethionate 2 | 5.4% | 5.4% |
| Sodium Cocoyl Glutamate | 0% | 0% |
| Sodium Laureth Sulfosuccinate | 3.04% | 5.40% |
| Cocamidopropyl Betaine | 0% | 0% |
| Cocamidopropyl Hydroxysultaine | 0% | 1.6% |
| Sodium Lauroamphoacetate | 0% | 0% |
| Lauric Acid | 2.4% | 2.4% |
| Lather Volume/Quality | Acceptable | Acceptable |
| Stability | Acceptable | Acceptable |
| Odor | Acceptable | Acceptable |

Table 7 demonstrates the flexibility of the invention with respect to the divalent anionic surfactant via replacing the acyl glutamate with sodium laureth sulfosuccinate, both in combination with a monovalent anionic as well as with replacement of the monovalent anionic.

Methods:
A). Lather Method and Evaluation
Lather was evaluated according to the following protocol:
Equipment: Sita Foam Tester R-2000
Standard Measurement Parameters:
Mixing Speed: 1000 rpm
Measurement time (Single timepoint): 45 Seconds
Dilution: 250 mL
Sample Size: 10 g
Procedure:
1) Run one cleaning cycle using hot tap water, in order to ensure vessel is clean, and to equilibrate temperature of vessel.
2) Fill Water Reservoir (Clear vessel on back of machine) with 38 C tap water. Ensure that water in vessel remains at 38 C+/−0.5 C for each measurement.
3) Weigh 10.0 g of product to be tested in a 10 mL syringe
4) Inject product to be tested into bottom of main vessel, being careful not to hit vessel walls or metal shaft in middle.
5) Check measurement parameters and enter in parameters defined above.
6) Begin measurement, record results
B). Stability Method

|  | Weeks | |
|---|---|---|
| Temperature | 1 | 2 |
| 4 C. | | |
| 25 C. | | |
| 37 C. | | |
| 45 C. | | |
| 50 C. | | |

Formulas must exhibit no crystallization at all of the above (bolded) temperature time points to be 'acceptable' in terms of stability.

C) Odor assessment Method
Sample placed in standard glass sample cup. Cap is removed and odor is assessed. Sample is compared with a control sample that is similar in age and handling conditions. Odor testing is carried out blinded by one familiar with the typical odor and characteristics of the formulation.

While this invention has been described with respect to particular embodiments thereof, it is apparent that numerous other forms and modifications of the invention will be obvious to those skilled in the art. The appended claims and this invention generally should be construed to cover all such obvious forms and modifications which are within the true spirit and scope of the present invention.

The invention claimed is:
1. A lamellar personal cleansing composition comprising:
1) 1 to 15% by wt. $C_8$ to $C_{20}$ acyl isethionate, the acyl isethionate being sodium cocoyl isethionate;
2) 0.5% to 12% by wt. acyl glycinate;
3) 0.5 to 12% by wt. acyl glutamate; and
4) 0.5 to 10% of an amphoteric surfactant; and
5) 1 to 5% by wt. lamellar structurant comprising lauric acid, lauryl alcohol or a mixture thereof,
wherein the amount by wt. of acyl glutamate in the composition as active, is greater than 50% the amount by wt. of acyl isethionate and chain length distribution of the acyl isethionate has $C_{12}$ chain within the chain length distribution between 60 to 72% and further wherein the composition has a pH between 6 to 8, a viscosity from 20,000 to 300,000 cP as measured by Brookfield viscometer T-A, 0.5 rpm, 60 seconds, and the composition comprises less than 3% by wt. of a sulfate surfactant.

2. The composition according to claim 1 comprising C8 to C18 chain length glycinate and wherein the amount of C12 to C18 glycinate is greater than 50% of the amount of C8, C10, and C12 to C18 chain length glycinate present.

3. The composition according to claim 1 wherein the composition comprises lamellar structurant present in an amount of 2 to 4 wt %.

4. The composition according to claim 1 comprising a thickener.

5. The composition according to claim 1 wherein said amphoteric surfactant is selected from the group consisting of alkyl amidopropyl betaine, alkyl amidopropyl hydroxysultaine, alkyl amphoacetate, and mixtures thereof.

6. The composition according to claim 1 wherein the glutamate is potassium cocoyl glutamate.

7. The composition according to claim 1 further comprising an emollient.

8. The composition according to claim 1 further comprising a cationic skin conditioning agent.

9. The composition according to claim 1 wherein the viscosity range of the composition is from 50,000 to 200,000 cP.

10. The composition according to claim 1 wherein the composition pH is from 6.5 to 7.5.

11. The composition according to claim 1 wherein the amphoteric surfactant is present from 1 to 6% by weight.

12. The composition according to claim 1 wherein the composition comprises less than 2% by weight of a sulfate surfactant.

13. The composition according to claim 1 wherein the composition comprises less than 1% by weight of a sulfate surfactant.

14. The composition according to claim 1 wherein the composition comprises sulfate surfactant.

15. The composition according to claim 1 wherein the composition has less than 3% by weight electrolyte.

16. The composition according to claim 1 wherein the composition has less than 1% by weight electrolyte.

* * * * *